United States Patent [19]

Wilson, Jr. et al.

[11] Patent Number: 4,713,343
[45] Date of Patent: Dec. 15, 1987

[54] BIODEGRADATION OF HALOGENATED ALIPHATIC HYDROCARBONS

[75] Inventors: John T. Wilson, Jr.; Barbara H. Wilson, both of Ada, Okla.

[73] Assignee: The United States of America as represented by the Administrator of the U.S. Environmental Protection Agency, Wahington, D.C.

[21] Appl. No.: 770,445

[22] Filed: Aug. 29, 1985

[51] Int. Cl.⁴ .............................. C02F 3/02; C02F 3/34; C12N 1/32; C12N 1/26
[52] U.S. Cl. .................................... 435/264; 435/247; 435/248; 435/250; 210/606; 210/611; 210/620
[58] Field of Search ............... 435/247, 248, 250, 262, 435/264; 210/606, 610, 611, 620, 627, 601

[56] References Cited

U.S. PATENT DOCUMENTS

| | | | |
|---|---|---|---|
| 3,979,283 | 9/1976 | Prudom | 210/611 |
| 4,385,121 | 5/1983 | Knowlton | 435/244 |
| 4,401,569 | 8/1983 | Jhaveri et al. | 210/610 |
| 4,447,541 | 5/1984 | Peterson | 435/264 |
| 4,452,894 | 6/1984 | Olsen et al. | 435/253 |

OTHER PUBLICATIONS

Stucki et al, Chemical Abstracts (1982), vol. 96, No. 7, p. 304, item #48791t.
Brunner et al. (1980), Applied and Environmental Microbiology, vol. 40, No. 5, pp. 950–958.
Monsen et al. (1984), Chemical Abstracts, vol. 101, No. 26, p. 270, item #234966a.
Parsons et al., J. Am. Water Works Assoc., vol. 76 (2), Feb. 1984, pp. 56–59.
Wilson et al., J. Environ. Qual., vol. 10, No. 4, 1981, pp. 501–506.
Wilson et al., EOS, vol. 64, No. 33, p. 505, Aug. 16, 1983.
Wilson et al., In Giuliano Ziglio, pp. 183–195, 1983, Monduzzi Editorie SPA, Bologna, Italy.
Love et al., J. Am. Water Works Assoc., vol. 74, Aug. 1982, pp. 413–425.
Bellar et al., J. Am. Water Works Assoc., vol. 66, Dec. 1974, pp. 739–744.
Bouwer et al., Appl. Environ. Microbiol., vol. 45, (4), pp. 1286–1294, Apr. 1983.
Wilson et al., Ground Water, vol. 21, No. 2, Mar.–Apr. 1983, pp. 134–142.
Wilson et al., Developments of Industrial Microbiology, vol. 24, pp. 225–233 (1983).
Hou et al., Applied and Environmental Microbiology, vol. 46, No. 1, pp. 171–177, Jul. 1983.
Haber et al., Science, vol. 221, pp. 1147–1153, Sep. 1983.

*Primary Examiner*—Esther M. Kepplinger
*Assistant Examiner*—William J. Herald

[57] ABSTRACT

Contaminating amounts of certain halogenated aliphatic hydrocarbons are degraded and removed from water such as drinking water and industrial waste water, by treatment of the water with a microorganism that is effective to metabolize gaseous hydrocarbons by the action of monooxygenase enzyme.

10 Claims, 1 Drawing Figure

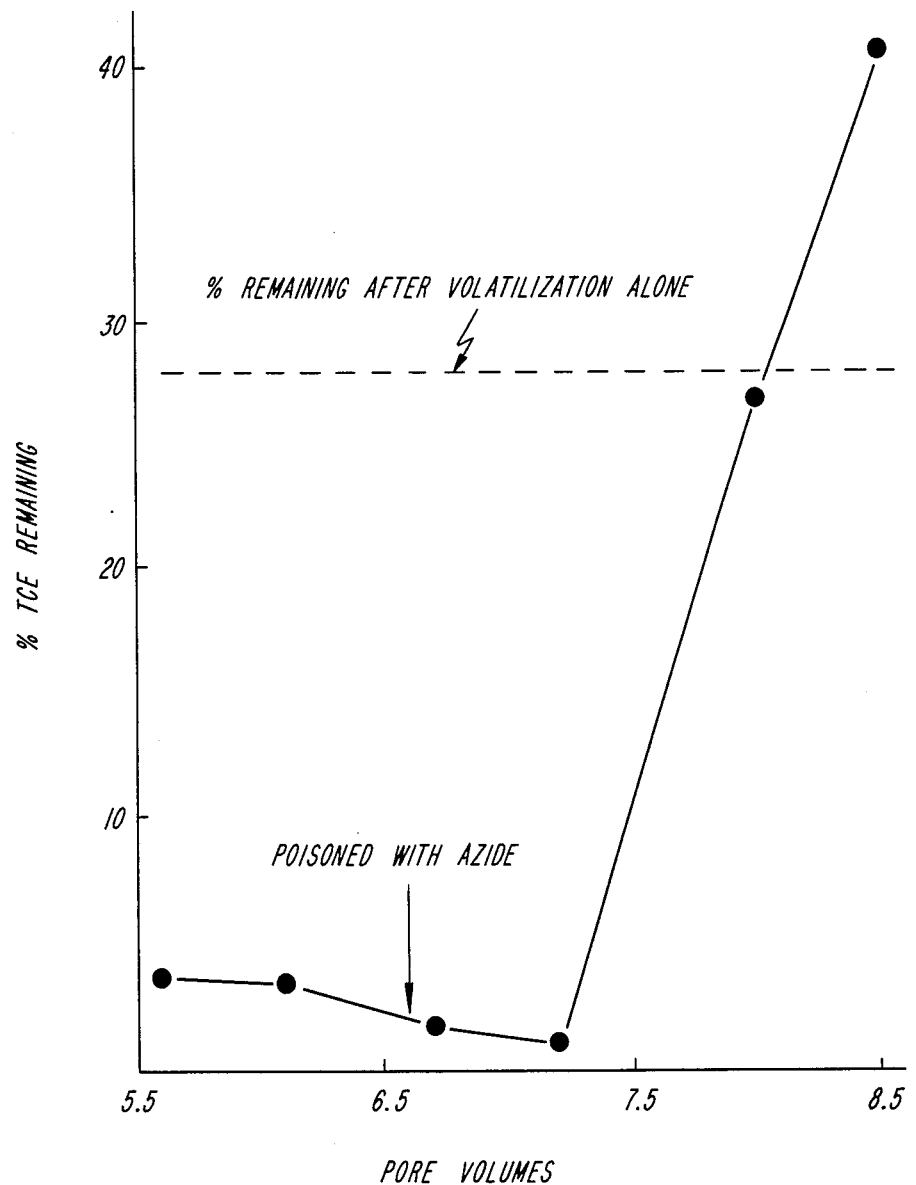

BIODEGRADATION OF HALOGENATED ALIPHATIC HYDROCARBONS

FIELD OF THE INVENTION

This invention relates to the aerobic biodegradation of certain halogenated aliphatic hydrocarbons and more particularly to the biodegradation of unsaturated halogenated aliphatic hydrocarbons in aqueous systems by treatment of the aqueous system with microorganisms which have the ability to aerobically degrade low molecular weight alkanes.

BACKGROUND

There has been substantial work directed to procedures by which polluted water may be purified by the removal of halogenated organic components. Some of these processes involve the use of various types of microorganisms. For example, U.S. Pat. No. 4,401,569 to Jhaveri et al discloses methods and apparatus for treating ground water contaminated with halogenated hydrocarbon compounds. The process involves degradation of the halogenated hydrocarbons by a microorganism. In this process, growth of microorganisms is enhanced under controlled conditions by addition of nutrients and gases such as oxygen, nitrogen, carbon dioxide or a combination. Treated water carrying these microorganisms, nutrients and gases is then returned for recirculation through a contaminated area of ground to leach out and biodegrade contaminants deposited in the ground. This patent is primarily concerned with removal of hydrocarbons from contaminated ground and ground water. The Jhaveri process uses the hydrocarbon as the feed stock; that is, the hydrocarbon provides the carbon and energy to support the growth of the active microorganisms. The only compounds which will support the growth of microorganism in this process are those that are capable of serving as a sole carbon and energy source.

U.S. Pat. No. 3,979,283 to Prudom discloses a process for the microbial degradation of DDT (dichlorodiphenyl-trichloroethane) by contact with microorganisms. However, the work in this patent is limited to aromatic halogenated hydrocarbons which are degraded with the non-pathogenic, hydrocarbon utilizing strains of Nocardia, Candida and Penicillium species. A similar disclosure may be found in U.S. Pat. No. 4,447,541 to Peterson which discusses various methods for biological decomposition of polyhalogenated organic compounds (PCB's) by treatment with microorganisms of the Pseudomonas type under special conditions of soil pH.

U.S. Pat. No. 4,452,894 to Olsen et al and No. 4,385,121 to Knowlton also disclose the degradation of hydrocarbons and halogenated aromatic hydrocarbons, respectively, using aerobic methods.

A substantial problem in this area is the contamination of drinking water by halogenated hydrocarbons which heretofore appeared non-biodegradable. Compounds such as trichloroethylene, tetrachloroethylene, carbon tetrachloride, 1,1,1-trichloroethane, vinyl chloride, 1,2-dichloroethane, and the like are especially difficult to remove from water. The extent of contamination in industrial regions is suggested from a survey of the State of New Jersey (Tucker, "Groundwater Quality in New Jersey: an Investigation of Toxic Contaminants"; Available from Office of Cancer and Toxic Substances Research, New Jersey Department of Environmental Protection). This study showed that more than a quarter of the wells sampled contained detectable concentrations of halogenated aliphatic compounds, a tenth had concentrations in excess of 10 ug/l, and one to two percent had concentrations in excess of 100 ug/l. The "Safe Drinking Water Act" (42 USC 300) requires the Environmental Protection Agency to establish primary drinking water regulations. One of the aspects of these regulations is to establish a maximum contamination level of halogenated organic materials such as those mentioned above. Proposed rules for drinking water regulations were published in the Federal Register, Volume 49, No. 114, 24329–24355, June 12, 1984.

The proposed Recommended Maximum Contaminant Levels (RMCL's) are zero for trichloroethylene, tetrachloroethylene, and carbon tetrachloride, and 200 ug/l for 1,1,1-trichloroethane.

Substantial work has been carried out to determine the levels of contaminants of this type, together with attempts as to how such contaminants may be removed. For example, Parsons et al, J. Am. Water Works Assoc., Vol. 76 (2), February 1984, pages 56–59, studied the contamination of drinking water by trichloroethene, which is a compound used as a drycleaning solvent. Wilson et al, J. Environ. Qual., Volume 10, No. 4, pages 501–506, 1981, discusses a study of the vulnerability of ground waters to pollution by organic chemicals that migrate through the soil, including various halogenated hydrocarbons. This article concluded that most low molecular weight halogenated aliphatic hydrocarbons were transported readily through the soil, which explained the increasingly frequent occurrence of these compounds in ground water.

In a publication by Wilson et al, EOS, Vol. 64, No. 33, page 505, Aug. 16, 1983, the authors studied the biological transformation of organic pollutants in ground water, and particularly the biotransformations of organic pollutants in the deeper subsurface environment. It was concluded that the rate of transformation is limited by the numbers and activity of microorganisms available, while the extent of transformation is most frequently limited by some requirement for metabolism such as oxygen, pH buffering capacity or mineral nutrients. In Table 2 of this publication the authors also set forth their opinion as to prospects for biotransformation of several important classes of organic pollutants found in ground water. The predictions were based on a cautious extrapolation from the behavior of the compounds and other natural systems. In general, the authors concluded as may be noted from Table 2 of that publication that for many halogenated aliphatic hydrocarbons there was no prospect of biotransformation in water table aquifers.

A further study was reported by Wilson et al, In Giuliano Ziglio, page 183–195, 1983, Monduzzi Editorie SPA, Bologna, Italy, wherein it was reported that, in general, halogenated aliphatic hydrocarbons are resistent to biodegradation in aerobic subsurface environments and this contributes to their persistence in polluted ground waters.

In a publication by Love et al, J. Am. Water Works Assoc., Vol. 74, August 1982, pages 413–425, there is set forth the results of studies on laboratory and pilot scales to ascertain the effects of aeration, adsorption and boiling for the removal of volatile organic solvents from water. None of these methods appear to be satisfactory for the removal of certain of these volatile materials.

Other work has included qualitative and quantitative studies with respect to the amount of volatile organic compounds of this type which may be contained in the soil or in the water. For example, in a publication by Bellar et al, J. Am. Water Works Assoc., Vol. 66, December, 1974, pages 739–744, the authors describe a method for the quantitative recovery of volatile organic compounds including chlorinated organic solvents from waste water using gas chromatographic procedures.

Studies have also been carried out with respect to possible transformation of halogenated aliphatic compounds using various bacteria. For example, in a publication by Bouwer et al, Appl. Environ. Microbiol., Volume 45, (4), pages 1286–1294, April, 1983, the transformation of 1- and 2-carbon halogenated aliphatic organic compounds was studied under methanogenic conditions. These authors concluded that several 1- and 2-carbon halogenated aliphatic organic compounds which were present at low concentrations in ground water were degraded under methanogenic conditions in batch baterial cultures and in a continuous flow methanogenic fixed film laboratory scale column. The authors suggest that transformation of halogented aliphatic compounds can occur under methanogenic conditions in the environment, but it was their conclusion that degradation of halogenated aliphatic compounds did not occur under the aerobic conditions of the study.

Many studies have been made with respect to bacteria contained in water of various types. Thus, in a publication by Wilson et al, Ground Water, Volume 21, No. 2, March–April, 1983, pages 134–142, the authors studied the enumeration and characterization of bacteria which are indigenous to a shallow water table aquifer. The goal of this study was simply to determine the bacteria present in such environments. In these studies concentrations of various halogenated organic volatile materials were determined and their degradation by bacteria contained in water table aquifers were then measured. The conclusions were that certain materials were degraded slowly and others were not degraded at all. For example, there was no detectable degradation of 1,2-dichloroethane, 1,1,2-trichloroethane, trichloroethylene or tetrachloroethylene. A similar report is described by Wilson et al in Developments of Industrial Microbiology, Vol. 24, p. 225–233 (1983).

In none of the prior art of which Applicants are aware are there successful procedures for degradation of certain low molecular weight halogenated aliphatic hydrocarbons, and particularly unsaturated chlorinated hydrocarbons under aerobic conditions. The present invention provides a solution to this problem.

SUMMARY OF THE INVENTION

It is accordingly one object of the invention to provide a method for the degradation of certain low molecular weight halogenated aliphatic hydrocarbons under aerobic conditions so as to degrade and effectively remove these halogenated aliphatic hydrocarbons from water.

A further object of the invention is to provide a method for the purification of water including purification of ground water.

A still further object of the invention is to provide a method for the aerobic degradation of low molecular weight chlorinated aliphatic hydrocarbons which are contained in aqueous systems by the use of microorganisms which have the capacity to metabolize gaseous hydrocarbons.

Other objects and advantages of the present invention will become apparent as the description thereof proceeds.

In satisfaction of the foregoing objects and advantages, there is provided by this invention a process for the removal of low molecular weight halogenated aliphatic hydrocarbons from water, which comprises treating the water with organisms which have the capability to aerobically degrade low molecular weight hydrocarbons by the action of a monooxygenase which produces the corresponding alcohol.

BRIEF DESCRIPTION OF THE DRAWINGS

Reference is now made to the drawing accompanying the application which illustrates the effective degradation of trichlorethylene in accordance with the process of the invention.

DESCRIPTION OF PREFERRED EMBODIMENTS

The present invention is concerned with methods for the aerobic degradation of low molecular weight halogenated aliphatic hydrocarbons, and especially chlorinated aliphatic hydrocarbons, to effectively remove these contaminating materials from aqueous systems. The aqueous systems with which the invention is concerned include drinking water as well as ground water, industrial waste waters and waters such as those produced by an interdiction well designed to intercept and remove a plume of contaminated ground water. The invention is particularly applicable to the treatment of ground water either in situ or by removal of a portion of the water, subjecting it to treatment and then returning the water to its environment. Broadly, however, the invention is concerned with the treatment of water regardless of its location or source to remove the indicated contaminants.

The invention is considered to be particularly suitable for improvements in the purities of ground water and drinking water by the removal of certain low molecular weight halogenated aliphatic hydrocarbons so as to cause contaminated water to conform to the requirements of the Safe Water Drinking Act as discussed above. No methods have previously been reported in the prior art for removal or degradation of these halogenated aliphatic hydrocarbons.

According to the present invention, it has been discovered that certain bacteria as described hereinafter will aerobically degrade low molecular weight halogenated aliphatic hydrocarbons. Compounds contained in water which may be degraded by the method of the invention include, in particular, trichloroethylene, 1,1,2-trichloroethane, dichloromethane, chloroform, 1,1-dichloroethane, 1,2-dichloroethane and cis-1,2-dichloroethylene, trans-1,2-dichloroethylene, 1,2-dibromoethane and vinyl chloride. The process is particularly satisfactory in the degradation of unsaturated aliphatic halogenated hydrocarbons. This group of compounds is ordinarily resistant to biodegradation in aerobic subsurface environments, as disclosed in the prior art publications mentioned above, and this characteristic contributes to their persistence in pollution of ground waters. While there is some consideration in the art with regard to biotransformation of these compounds in anaerobic subsurface materials, the transformations are often incomplete, and occasionally result in the accumulation of products that are as much a problem as the original contaminants, such as the conversion of trichloroethylene or tetrachloroethylene to vinyl chloride.

The current technology for reclaiming ground water polluted with these compounds primarily involves pumping the water to the surface and either stripping out the compounds in aeration towers or removing the pollutants on some type of sorbing material. The present invention, however, provides a method for treatment of contaminated water which can be carried out in situ so as to result in destruction of the contaminants rather than simple transfer to another environmental medium. This process thus has substantial economic and environmental advantages which are applicable directly at the pollution site.

The effective aerobic agent of the present invention comprises organisms which will metabolize low molecular weight hydrocarbons using a class of enzymes called monooxygenases. The bacteria or microorganisms used in the present invention are those bacteria which have the capability to aerobically degrade low molecular weight alkanes by beginning their attack with the action of a monooxygenase which produces the corresponding alcohol. Apparently these monooxygenases have low specificity and will accept a variety of compounds.

As a class, the microorganisms for use in the present invention are those microorganisms which proliferate in the soil when exposed to a mixture of a low molecular weight hydrocarbon and oxygen. Low molecular weight hydrocarbons include methane, ethane, n-propane, n-butane or mixtures thereof. The oxygen is preferably supplied as air but pure oxygen may be used. Also, other substances may be used which liberate oxygen such as hydrogen peroxide.

The present invention takes advantage of the metabolic activity of these indigenous microorganisms, in order to aerobically degrade certain halogenated aliphatic hydrocarbons, and particularly chlorinated ethanes and ethenes of this class. As indicated above, these bacteria apparently aerobically degrade low molecular weight alkanes by beginning their attack with the action of monooxygenase to produce the corresponding alcohol. They appear to have low specificity and accept a variety of compounds. Further, the monooxygenase of propane-grown bacteria transforms ethylene to ethylene oxide, which in turn is further degraded.

The process can occur in any material that can be colonized by alkane oxidizing bacteria. Oxygen, either in pure form or as air or other admixture, or oxygen-liberating substance, together with an alkane, and optionally an inoculum of appropriate bacteria, is added to the water to be treated. On proliferation of the alkane oxidizing bacteria, the halogenated aliphatic hydrocarbon is degraded. The only product of degradation which can be identified is carbon dioxide.

There are a number of procedures which have been theoretically proposed for the enhancement of indigenous microorganisms to encourage biological transformation of pollutants. However, all of these, such as the process of Jhaveri et al, U.S. Pat. No. 4,401,569 discussed above, appear to involve the addition of dissolved oxygen, nitrogen, phosphorus, sulfur, iron magnesium, calcium, or other inorganic nutrient which stimulates general microbial activity by supplying nutrients which are inadequately available to cause microbial activity. In contrast to these types of processes, the method of this invention involves the unique addition of an oxygen or an oxygen containing compound and an organic material, i.e., an alkane, to stimulate the activity of specific microorganisms which will biodegrade specific materials; that is, halogenated aliphatic hydrocarbons such as trichloroethylene. The method degrades these halogenated aliphatic compounds aerobically without the production of byproducts which are in themselves unwanted materials. Thus, the products from the process of this invention are carbon dioxide and water so that the halogenated organic compound is removed from the water.

Microorganisms of this type used in this invention are described, by Hou et al, for example, in Applied and Environmental Microbiology, Volume 46, No. 1, pages 171–177, July, 1983. The agents are described in this publication as being effective to epoxidize ethylene. They are also described as bacteria that can use as the sole sources of carbon and energy, 1-carbon compounds, thus the name methanotrophic bacteria. Methanotrophic bacteria, their biochemical diversity and genetics are described by Haber et al, Science, Volume 221, pages 1147–1153, September, 1983. Methanotrophic bacteria as described by Haber et al designate bacteria that can use methane to produce carbon and energy. As described by Haber et al, approximately 50% of the organic carbon which is degraded anaerobically is converted to methane, most of which is oxidized by methanotrophs to carbon dioxide before it reaches the atmosphere. In aquatic environments Haber et al points out that these microbes are numerous in regions where methane produced from anaerobic decomposition of organic matter and oxygen from the atmosphere are present at concentrations optimal for their growth. The entire disclosures of the Hou et al and Haber et al publications are hereby incorporated by reference in their entirety as disclosing known sources and characteristics of the microorganisms of the invention.

While Hou et al, Haber et al and Bouwer et al, Appl. Environ. Microbiol., Vol. 45 (4), pages 1286–1294, April, 1983, all recognized that compounds of this type may be biotransformed by anaerobic materials such as acetate degrading methanogens, it was unexpected that such processess would be effective in subsurface materials, since transformations of these types are often incomplete and occasionally result in the accumulation of unwanted products. It was therefore unexpected that the process of the present invention would be operable to provide excellent results in biodegradation of halogenated aliphatic compounds in aerobic subsurface environments.

The microorganisms used in the present invention have been identified in the art and the methanotrophs, for example, have been identified by their wide-spread distribution, their taxonomic diversity and their physiological properties. They are described for example by Colby et al, Annu. Rev. Microbiol., Vol. 33, page 481, 1979; by Hansen in Adv. Appl. Microbiol., Vol. 26, 3, 1980; and Higgins et al, Microbiol. Rev., Vol. 45, 556, 1981. The bacteria are all gram negative, obligate aerobes and exist in a variety of shapes, such as rods, vibrios and cocci. These bacteria are numerous in aquatic environments at concentrations optimal for their growth.

In conducting the process, the bacteria contained in water are treated with oxygen or air and a low molecular weight alkane. Exposure of the microorganisms to the mixture of aliphatic alkane and air will cause the bacteria to proceed with degradation of certain halogenated aliphatic compound present in the water. In practical operation, it is preferred in one embodiment to treat the water with a stream of air which contains a mixture of the lower alkane and also contains oxygen. For example, a mixture of natural gas and air is satisfactory and a preferred method is to contact the water to cause the microorganisms to aerobically degrade the halogenated aliphatic hydrocarbon. A period of time will be necessary for acclimation of the microbes to the mixture of alkane and oxygen.

The process is operable to degrade halogenated aliphatic hydrocarbons at concentrations of up to 200 micrograms per liter, and has been operated satisfactorily at concentrations of 200 micrograms per liter and 30 micrograms per liter of trichloroethylene. The solubility of oxygen itself may be too low to permit complete degradation of saturated solutions of methane, n-butane, or n-propane. Hydrogen peroxide or other oxygen source can be added in order to achieve complete oxidative metabolism of the alkane.

The invention may be practiced by treating water in situ or by removing the water and treating by the process of the invention and then returning the water to its environment. Obviously, however, since removal of water from its environment for treatment is an expensive procedure, and an advantage of the present invention is that water such as ground water may be treated in situ by addition of a solution of low molecular weight alkane and oxygen or substance which will liberate oxygen to achieve the degradation of the contaminating compounds.

For in situ reclamation, the oxygen and the hydrocarbon to support growth must be dissolved in the water. In actual tests in aquifer microcosms containing approximately 30 mg/L oxygen and 7 mg/L methane, methanotrophs degrade roughly half of the trichloroethylene present, regardless of the initial trichloroethylene concentration, over a range of 10 to 1,000 u/L of trichloroethylene. Extensive removals of trichloroethylene in situ would probably require repeated treatments with solutions of oxygen and the gaseous hydrocarbon. In one test of microcosms constructed from aquifer material, acclimation of organisms required about 4 weeks. In another test of microcosms constructed from aquifer material, acclimation was well along in only 10 days. Accordingly, results may vary depending on the contaminated water source.

There are several ways the process can be carried out in the field. Thus, if a plume originates from a source that cannot be terminated, such as a sensitive military installation or an active factory, injection wells can be installed across the plume for injection of concentrated solutions of gaseous hydrocarbons and other solutions of pure oxygen or hydrogen-peroxide. Dispersion would mix the injected waters with the plume, allowing the microbes to reduce the concentration of the contaminant.

In a different situation, contaminated water can be pumped to the surface, treated with hydrocarbon and oxygen, then re-injected either in the same well or another well. The renovated water can be recovered from the injection well in a fill-and-draw cycle, or it can be drawn to a second recovery well on a continuous basis.

The following examples are presented to illustrate the invention, but it is not to be considered as limited thereto. In the examples, parts are by weight unless otherwise indicated.

EXAMPLE 1

In this example, water containing known amounts of trichloroethylene was subjected to the process of the invention. In the method, sandy soil was packed into a glass column to a depth of 150 cm. Then water containing trichloroethylene was applied at the rate of 21 cm per day. The elution volume of the column was 41 cm of water. Water entering and leaving the column passed through 16 ml screw cap test tubes that were sealed with a Teflon faced septum. As appropriate, the tubes were removed for analysis of trichloroethylene according to the United States Environmental Protection Agency test method No. 601, (U.S. Environmental Protection Agency, 1982, Methods for Organic Chemical Analysis of Municipal and Industrial Waste Water, EPA 600/4-82-057, Environmental Monitoring and Support Laboratory, Cincinnati, Ohio 45268). The tubes were then left in place long enough for 15 to 25 flushings before the samples were taken. With the exception of the sampling method, the construction and operation of the column was the same as described by Wilson et al, J. Environ. Qual., Volume 10, pages 501-506, 1981.

A stream of air containing 0.6 percent natural gas by volume was passed over the head of the column. Three weeks were allowed for acclimation, after which the soil received water which contained trichloroethylene at an average concentration of 150 micrograms per liter. The concentrations of the trichloroethylene in the column effluent were then monitored for two weeks. The removal of trichloroethylene was extensive, with less than 5 percent of the applied trichloroethylene passing through the soil. See the graph accompanying the application. This contrasts sharply with the breakthrough of 28 percent of applied trichloroethylene in our earlier work, where volatilization was the only removal process, (Wilson et al, J. Environ. Qual., Volume 10, pages 501-506, 1981).

To confirm that the increased removal represented biological activity, the column was poisoned with water that contained 224 micrograms per liter of trichloroethylene and 2 grams per liter of sodium azide. As will be noted from the graph accompanying the application, breakthrough of the trichloroethylene increased dramatically.

EXAMPLE 2

In an attempt to identify the products of the biotransformation, a second column was acclimated to natural gas, then dosed with a solution of $14_C$-trichloroethylene. After 1.6 solution volumes of water had been applied, 15.8±0.3 percent (alpha=0.05) of the applied radiolabel appeared in the column effluent. This label could not be purged from the solution by vigorous aeration when the pH was adjusted to 11. At least 97 percent (alpha=0.05) of the label was purged when the pH was adjusted to 2 and at least 93 percent (alpha=0.05) of the label precipitated with barium hydroxide. Apparently, the trichloroethylene degraded to carbon dioxide.

The biological activity lowered the concentration of the trichloroethylene roughly an order of magnitude during the two day residence time of water in the column. A rate of this type is adequate for in situ reclamation.

EXAMPLE 3

In this example, there is set forth the rate of attack and results on twelve halogenated aliphatic hydrocarbons contained in aerobic sand soil. The experimental conditions were as set forth in Example 1. The top 10 cm of soil in the column contained from ten million to 100 million bacteria per gram. These conditions can be taken as a lower limit on the rate of treatment in a surface-based treatment system (as in the soil column) where the contaminated water is exposed to a mixture of gaseous hydrocarbons in air. The combustion of a volume of methane requires about 2 volumes of pure oxygen. Because air is 20% oxygen, combustion of a mixture of 9–10% methane in air would result in the near complete removal of both gases. There was used 0.6% methane in air in order to be well below the lower explosive limit for methane in air. The results are set forth in the following table:

| Compound | % Removed[a] | Rate of Removal[b] $hr^{-1}$ | Rate of Removal at 95% Confidence $hr^{-1}$ |
| --- | --- | --- | --- |
| Trichloroethylene (TCE) | 95 | 0.95 | 0.75 |
| Trans - 1,2 Dichloroethylene | >94 | >0.86[c] | — |
| Cis - 1,2 Dichloroethylene | >98 | >1.2[c] | — |
| 1,2 - dibromoethane (EDB) | 94 | 0.86 | 0.42 |
| Dichloromethane | 94 | 0.91 | 0.41 |
| Chloroform | 83 | 0.55 | 0.29 |
| 1,2 - Dichloroethane | 85 | 0.60 | 0.56 |
| 1,1 - Dichloroethane | 76 | 0.44 | 0.41 |
| 1,1,2 - Trichloroethane | 55 | 0.25 | 0.22 |
| 1,1,1 - Trichloroethane (TCA) | 19 | 0.067 | 0.023 |
| Carbon Tetrachloride | 44 | 0.18 | 0.13 |
| Tetrachloroethylene (PCE) | 31 | 0.11 | 0.085 |

[a]Material that passed through a living soil ÷ material that passed through soil killed with 0.1% sodium azide × 100.
[b]Assumes all the biological activity is uniformly distributed in the top 10 cm of soil.
[c]Concentrations were below detection units after passage through living soil.

As will be noted from the table, substantial amounts of most of the materials were removed or degraded by the process. All degradations were considered satisfactory to excellent except for 1,1,1-trichloroethane, carbon tetrachloride, and tetrachloroethylene which were less than 50% degraded.

The invention has been described herein with reference to certain preferred embodiments. However, as obvious variations thereon will become apparent to those skilled in the art, the invention is not to be considered as limited thereto.

What is claimed is:

1. A process for the treatment of water which contains halogenated aliphatic hydrocarbons to aerobically degrade said halogenated aliphatic hydrocarbons, said halogenated aliphatic hydrocarbons being one or more members selected from the group consisting of 1,1,2-trichloroethane, 1,1-dichloroethane, 1,2-dichloroethane, trichloroethylene, cis-1,2-di-chloroethylene, trans-1,2-dichloroethylene, 1,2-dibromoethane, and vinyl chloride, the process comprising treating the water with a microorganism in the presence of a lower molecular weight alkane containing 1 to 4 carbon atoms, and oxygen, the microorganism comprising bacteria that can aerobically degrade low molecular weight alkanes by beginning their attack with the action of a monooxygenase to produce the corresponding alcohol, the bacteria acting to degrade said halogenated aliphatic hydrocarbons to form products comprising carbon dioxide and water.

2. A process according to claim 1 wherein the lower molecular weight alkane is methane, ethane, normal propane, normal butane or mixtures thereof.

3. A process according to claim 2 wherein the water is industrial waste water and the water is treated with the microorganism in situ.

4. A process according to claim 1 wherein the water is ground water and the contaminating halogenated aliphatic hydrocarbon is trichloroethylene.

5. A process according to claim 2 wherein the microorganism is a methanotroph and the process is carried out in the presence of a mixture of natural gas and air.

6. A process according to claim 1 wherein the water contains up to 200 micrograms per liter of said halogenated aliphatic hydrocarbons.

7. A process according to claim 1 wherein the water contains up to 30 micrograms per liter of trichloroethylene.

8. A process according to claim 1 wherein the water to be treated is industrial waste water.

9. A process according to claim 1 wherein the water to be treated is from an interdiction well.

10. A process according to claim 1 wherein the water is treated in situ.

* * * * *